United States Patent [19]

Landa et al.

[11] Patent Number: 4,989,932
[45] Date of Patent: Feb. 5, 1991

[54] MULTIPLEXER FOR USE WITH A DEVICE FOR OPTICALLY ANALYZING A SAMPLE

[75] Inventors: Isaac Landa, Potomac; Michael M. Anthony, Gaithersburg; George E. Toth, Colombia, all of Md.

[73] Assignee: LT Industries, Rockville, Md.

[21] Appl. No.: 318,246

[22] Filed: Mar. 3, 1989

[51] Int. Cl.$^5$ .............................................. G02B 6/00
[52] U.S. Cl. .............................. 350/96.1; 350/96.15; 356/440
[58] Field of Search ............... 250/227; 356/440, 441, 356/328; 350/96.1, 96.15, 96.2, 96.21

[56] References Cited

U.S. PATENT DOCUMENTS

| | | | |
|---|---|---|---|
| 3,350,156 | 10/1967 | Adams | 350/445 |
| 4,540,282 | 9/1985 | Landa et al. | 356/328 |
| 4,594,533 | 6/1986 | Snook et al. | 356/440 X |
| 4,626,065 | 12/1986 | Mori | 350/96.15 |
| 4,630,255 | 12/1986 | Gouali et al. | 350/96.15 |
| 4,636,028 | 1/1987 | Mori | 350/96.15 |
| 4,669,817 | 6/1987 | Mori | 350/96.15 |
| 4,699,766 | 10/1987 | Yamashita | 356/440 X |
| 4,744,617 | 5/1988 | Hvezda et al. | 350/96.15 |
| 4,848,871 | 7/1989 | Seidel et al. | 350/96.15 |

Primary Examiner—John D. Lee
Assistant Examiner—John Ngo
Attorney, Agent, or Firm—Saidman, Sterne, Kessler & Goldstein

[57] ABSTRACT

The invention is a multiplexer which enables light to be sent to and received from samples for simultaneous analysis. A multiplexer is described which uses a transverse probe to reflect light at an angle into an optical rod. The transverse probe is selectively rotated to transmit light to a second optical rod. Various numbers of optical rods may be used in the linear mutliplexer. A multiplexer is also described in which a conjugate optical barrel is utilized to selectively reflect light to various probes.

11 Claims, 2 Drawing Sheets

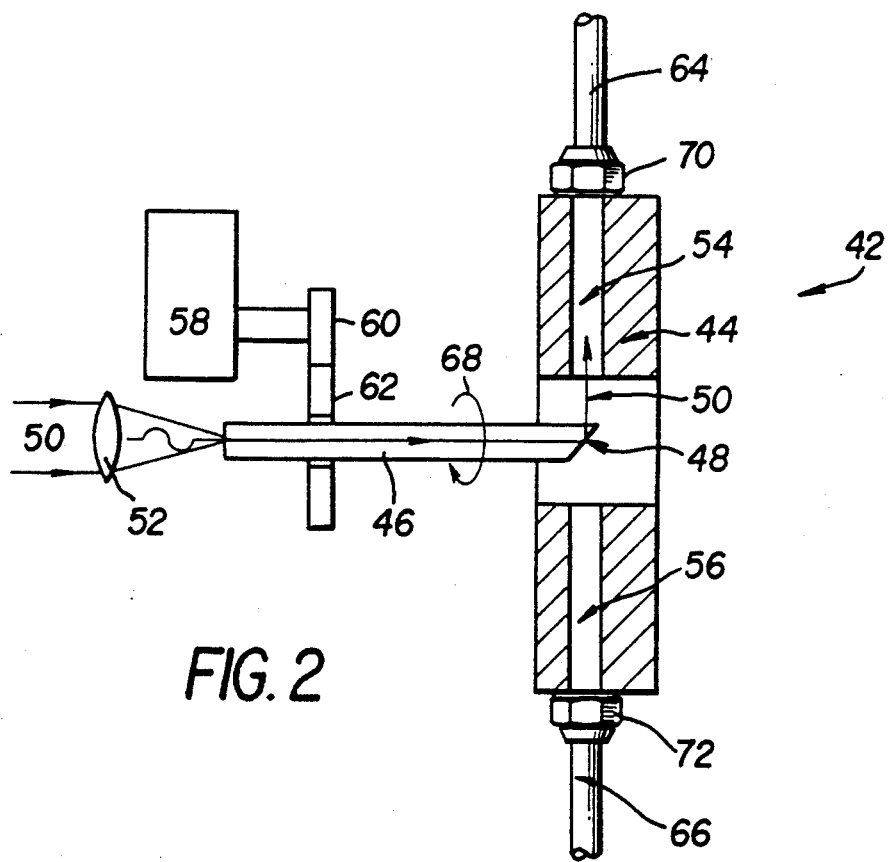
FIG. 2
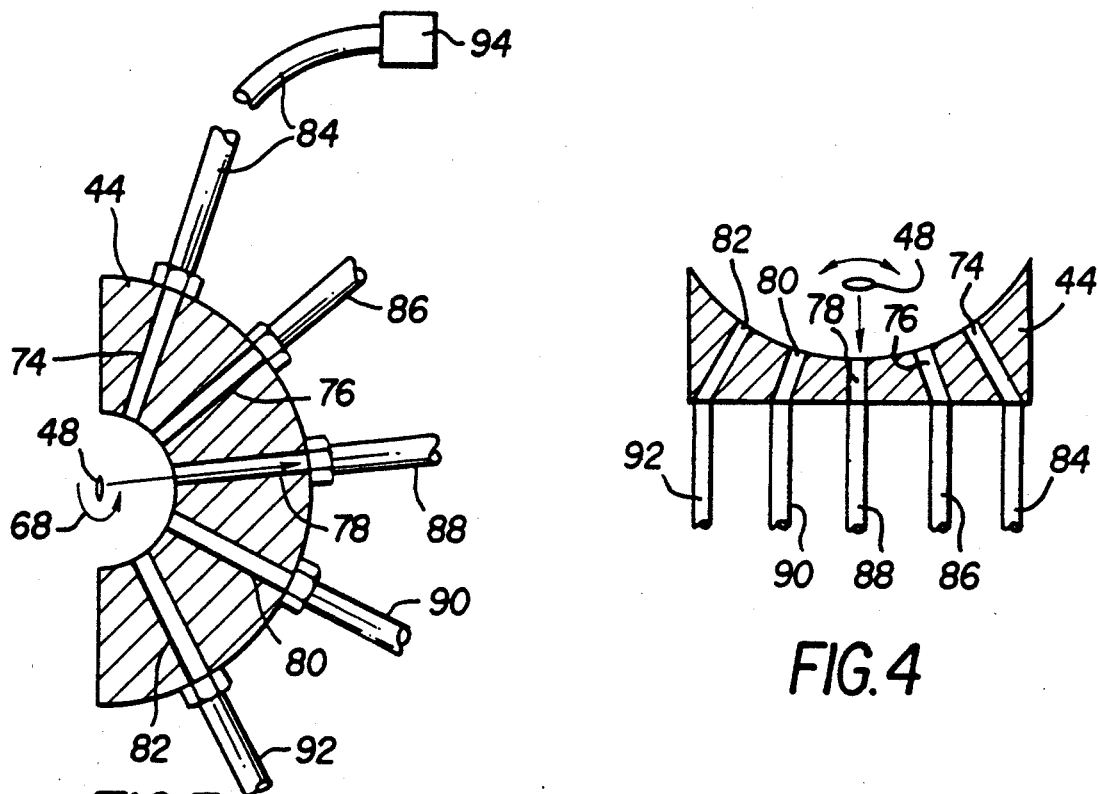
FIG. 3
FIG. 4

MULTIPLEXER FOR USE WITH A DEVICE FOR OPTICALLY ANALYZING A SAMPLE

BACKGROUND OF THE INVENTION

1. Field of the Invention

The present invention relates generally to a device for simultaneously analyzing samples and more particularly to a multiplexer which enables a plurality of samples to be analyzed using spectral analysis.

2. Background

U.S. Pat. No. 4,540,282 to Landa et al. (the Landa et al. patent) is an apparatus for optically analyzing a sample. The device described by the Landa et al. patent is an electro-optical system for rapid, accurate spectral analysis of the reflectivity and/or transmissivity of samples. In this device, a holographic defraction grating is oscillated at high speeds to provide a rapid scanning of monochromatic light through a spectrum of wavelengths. The grating drive system is an electrically driven mechanical oscillator which utilizes the back EMF of the oscillator motor to maintain oscillation at a desired amplitude and frequency. An optical shutter alternately blocks the light as the grating is oscillated.

The present invention is a device which may be used in conjunction with the device described by Landa et al. patent or similar devices in order to increase the productivity thereof and to eliminate the need for multiple optical analyzing devices.

It is one object of the invention to provide a multiplexer which allows the analyzation of several samples substantially simultaneously.

It is yet another object of the invention to provide a multiplexer having a small path length so that any variation or movement in the optics will not result in a magnification thereof.

It is yet another object of the invention to have a multiplexer which is small and compact in size.

SUMMARY OF THE INVENTION

In accordance with the purposes of the present invention as embodied and described herein, the present invention is a multiplexer for use with a apparatus for optically analyzing a sample. This multiplexer includes a body portion having a primary light inlet port. The light received through the light inlet port is deflected orthogonally by a first mirror which directs light to a first exit port of a plurality of pairs of ports. The light exiting the first exit port of a plurality of pairs of ports is returned to the multiplexer by a second port of the plurality of pairs of ports. The light passing through the second port is deflected orthogonally so that the light is travelling in substantially the same direction as the light passing through the primary inlet port. The light then exits the body through a primary exit port. The first mirror and the second mirror are rotatably mounted within said body and movable to a second set of a plurality of inlet and exit ports.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 2 is an alternate embodiment of the multiplexer of the present invention.

FIG. 3 is an alternate embodiment of the multiplexer of the present invention.

FIG. 4 is an alternate embodiment of the multiplexer of the present invention.

DETAILED DESCRIPTION OF THE PREFERRED EMBODIMENTS

Figure 1:
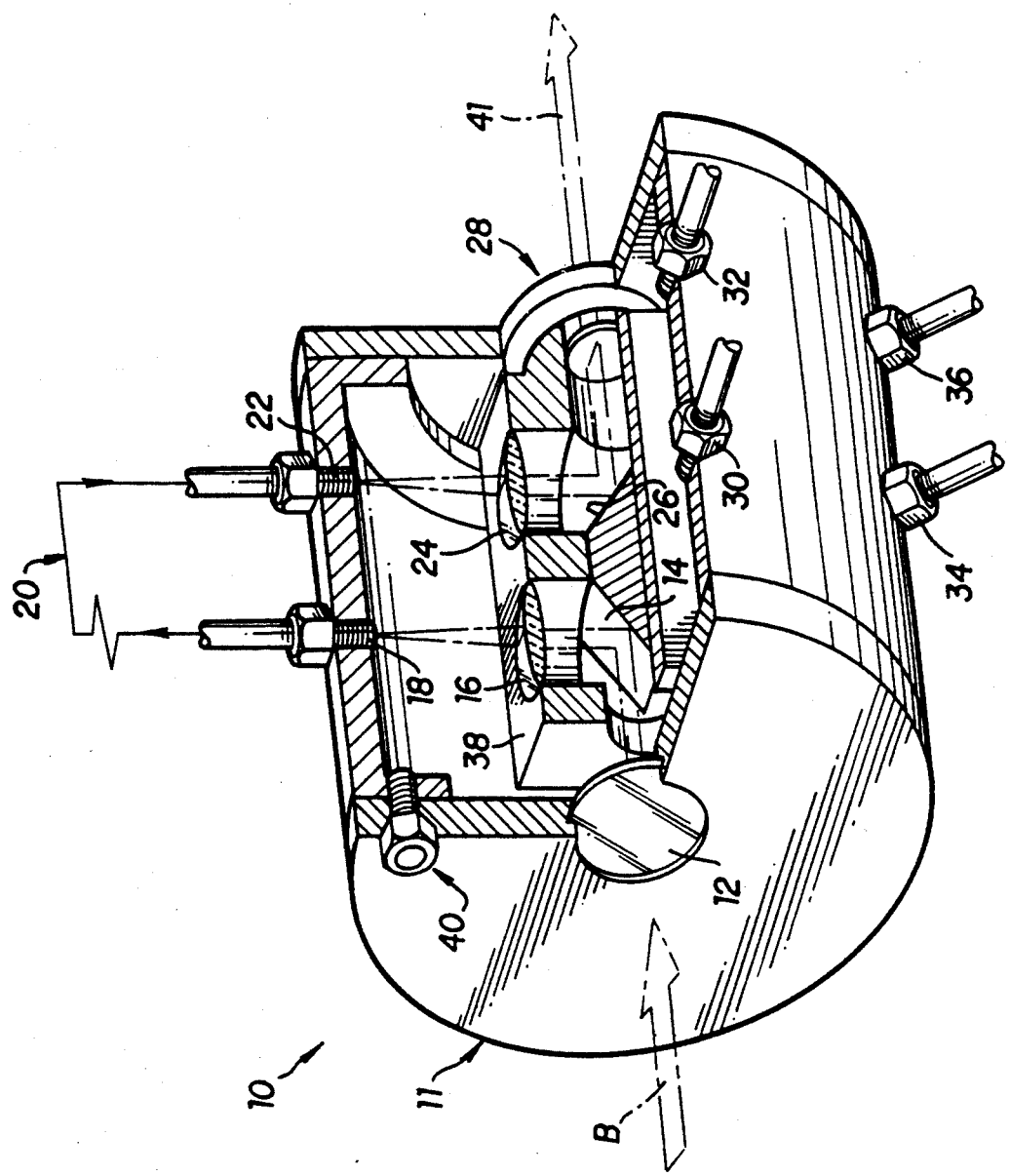
FIG. 1 is a perspective view of the multiplexer of the present invention.

The present invention is a multiplexer for use with an apparatus for optically analyzing a sample such as the device disclosed in U.S. Pat. No. 4,540,282 to Landa et al. The disclosure of the Landa et al. patent is herein incorporated by reference and forms a part of this specification. The multiplexer shown generally as 10 includes a body portion 11 which may be cylindrically shaped as shown in FIG. 1. Light is introduced into multiplexer 10 via a primary inlet port 12. The device which is described by the Landa et al. patent is one device which is particularly useful in conjunction with this multiplexer; however, other devices for optically analyzing a sample may be used in conjunction with the multiplexer of the present invention.

The Landa et al. patent describes an electro-optical system which determines the reflectivity and/or transmissivity of samples. In order to spectrally analyze a sample, a light dispersing element such as a holographic defraction grating is sinusoidally oscillated at a preselected high speed to provide a rapid scanning of monochromatic light through a selected spectrum of wave lengths. Light which is down stream of the defraction grading passes through an exit slit which may be adjustable to enable selection of an optimal spectral band width for a particular application. Light passing through such an exit slit may then be passed into the multiplexer 10 of the present invention. Such light depicted by arrow 13 passes through primary inlet port 12. The light is then deflected by a first mirror 14 orthogonally and focused by a focusing lens 16 onto the end of a fiber optic bundle (not shown) or other light transmitting device. The light which passes through the focusing lens also passes through a first exit port 18 as shown in FIG. 1. After passing through the first exit port, the light is transmitted through fiber optic bundles or the like to a sample.

There are three modes in which a device of the type described by the Landa et al. patent may operate. In the first mode the light passes through the fiber optic bundle and through a probe which may be in light communication with the sample. In this mode, the reflectance mode, light reflects from the sample, back into the probe and through the fiber optic bundle. A bidirectional fiber optics configuration is used to allow light to pass through the fiber optics bundle in both directions simultaneously. The light being passed back through the fiber optic bundle is then passed through first inlet port 22.

The second mode of operation is the transmittance mode. In this mode, light passes through fiber optic bundles through a probe which transmits light through a sample. A second probe then receives the transmitted light and passes it back through a fiber optics bundle through first inlet port 22.

In the third mode of operation, the transflectance mode, light passes through a fiber optics bundle to a probe. Part of the light emanating from the probe will be reflected back through the probe and through the fiber optics bundle. The remaining light will be transmitted through the sample and reflected back through the sample via a mirror or other means for reflecting light. This reflected light will pass through the sample and again pass through the probe and through the fiber optics bundle to be analyzed. Both the light which is reflected from the sample and transmitted through the sample will pass through first inlet port 22.

Regardless of the mode of operation of the fiber optics and probe, the multiplexer operates in the same way. Whether the device is operating in a reflectance mode, a transmittance mode, or a transfectance mode, the light leaves the multiplexer through an exit port (either 18. 30 or 34) and returns through an inlet port (either 22, 32, or 36). The light returning through inlet port 22 may pass through a focusing lens or the like 24 and is reflected by a second mirror 26. It should be noted that the first mirror 14 ° nd the second mirror 26 may either be separate reflective members which are glued or otherwise attached to an angled surface or may be simPly a polished surface of the angled portion of the conjugate optical barrel 38. Details of the optical barrel 38 will be discussed below. Light which is reflected through a 90° angle by mirror 26 exits multiplexer 10 through a primary exit port 28. The light exiting the multiplexer 10, shown generally as 42 is then analyzed by an apparatus for optically analyzing a sample such as the device described in the Landa et al. patent.

The construction of the present invention enables multiplexing, the sampling of a number of different products simultaneously. This is possible because of a conjugate optical barrel 38 which is rotatable about the axis of the body portion 11 of multiplexer 10. As seen in FIG. 1, the light passes through ports 18 and 22. However, by rotating the conjugate optical barrel 38 it can be seen that the light would exit through a second exit port 30 and return to the multiplexer via second inlet port 32. Similarly, when the conjugate optical barrel 38 is further rotated, the light would pass through third exit port 34 and return to the multiplexer 10 via third inlet port 36. While the embodiment shown in FIG. 1 shows only three sets of ports, it is contemplated that a number of ports may be used to practice the invention.

The multiplexer shown in FIG. 1 has multiple channels so by rotating the conjugate optical barrel, along with the lenses and the reflective mirrors, the beam which leaves the multiplexer can be picked up by whatever channel the user desires. By rotating the conjugate optical barrel, the light which exits through the primary exit port will pass to the optical analyzer in the same way.

To practice this aspect of the invention a stepper motor may be attached to the conjugate optical barrel. This stepper motor can access each set of ports randomly and may idle on each set of ports according to the requirements of the user. In order to accomplish such a result, conventional electronics and software may be used.

In order for the stepper motor to stop at the exact necessary position, reference holes may be placed in the walls of body portion 11. A light emitting diode (LED) or the like may be used to emit a light signal. When the light of the LED passes through the small holes, one corresponding to each channel of the multiplexer, a signal can be relayed to the stepper motor so that the motor will stop at an exact point. Although a hole in the side of the body portion 11 is preferably only about 20 mils in diameter, the hole may nevertheless be too large for the conjugate optical barrel to stop at precisely the proper point for proper focusing upon the fiber optical bundles. In order to solve this problem it may be necessary to control the motor by looking for the point at which the intensity through the hole is a maximum. The light intensity passing through the hole will be parabolic in profile. By finding the point at which the intensity is greatest, it is possible to stop the motor at precisely, or nearly precisely the proper point so that the light passing through exit ports 18, 30, or 34 will proper be focused upon a fiber optics bundle. The first step in determining the proper spot to spot might require calibration of the profiles of the light intensity of the LED.

In another aspect of the invention a linear multiplexer is provided. This multiplexer will be discussed with reference to FIG. 2.

Turning to FIG. 2, a linear multiplexer 42 is shown which enables remote measurements using an analyzer such as that described by the Landa et al. patent. Such a linear multiplexer allows simultaneous analysis of a plurality of samples. The linear multiplexer 42 as herein described is designed to have a short light path length and thus decreases the likelihood of errors. The linear multiplexer 42 has a body 44 which may be made out of a number of different materials such as stainless steel. In one preferred embodiment of the invention, the body 44 is a half disk, as shown in FIG. 3. Another embodiment of the body 44 is depicted in FIG. 4.

The linear multiplexer 42 utilizes a transverse Probe 46 which introduces light into one of a plurality of optical transmission rods 54 and 56. Light which passes through probe 46 is reflected by a mirrored surface 48 and thereby reflected. In the embodiment of the invention shown in FIG. 2, this reflection is orthogonal, as shown by the light stream 50. It should, however, be noted that there is no requirement that the light be deflected at an angle of 90°. Other angles may be equally suitable for practicing the invention. The light stream 50 is introduced to linear multiplexer 42 through a lens system shown generally as 52. The light stream 50 is focused onto the end of a transverse probe 46. This transverse probe may take on a number of different forms and modifications. However, in a preferred embodiment of the invention, the light is passed through an optical rod such as quartz or sapphire, which make up in part the transverse probe 46. Light passing through the probe is reflected by mirror 48 into one of a number of optical transmission rods 54 and 56. These optical transmission rods may be, for example, a solid quartz rod or a solid sapphire rod. In addition, it may be possible for these optical transmission rods 54 and 56 to be hollow with an interior reflective surface for propagating the light down the optical path. If the path length between the mirrored surface 48 and the fiber optic bundle 64 is short, it may be possible to eliminate the need for optical transmission rods. In FIG. 2, the light path 50 is shown to be traveling through optical transmission rod 54 and into fiber optic bundle 64. The fiber optic bundle is connected to the body 44 of the linear multiplexer 42 with a connector 70.

A stepper motor 58 is operatively connected to the transverse probe 46 by means of gears 60 and 62 which are schematically depicted in FIG. 2. This stepper motor 58 rotates the transverse probe 46 as indicated by arrow 68 The stepper motor rotates the transverse probe so that light is reflected and passed through optical transmission rod 56 rather than 54 as depicted in the drawings. Light which passes through optical transmission rod 56 then passes through optical fiber bundle 66 which is attached to the body 44 of linear multiplexer 42 by a connector 72. Light which passes through either optical bundle 64 or optical bundle 66 is reflected by and/or transmitted through a sample to be analyzed. The optical transmission rods 54 and 56 are preferably a simple, straight cylindrical form. The mirror or mirrored surface 48 is rotated by means of the stepper motor 58 and an optical encoder. Each rod is brought into focus by the action of the stepper on the rotating mirror. The optical encoder enables the stepper to rotate to a precise position. It should be noted that, through programming, the stepper motor may access different channels of the multiplexer randomly.

In the embodiment of the invention shown in FIGS. 3 and 4, a mirrored surface 48 directs light through optical transmission rods 74, 76, 78, 80 and 82 through corresponding optical fiber bundles 84, 86, 88, 90 and 92. In FIG. 3, a probe 94 is schematically shown which introduces light to the sample to be analyzed. The probe introduces light in one of three modes. The light can either be reflected by a sample and passed back through the optical fiber bundle. In this case, a bidirectional fiber optic arrangement is used. The light may also be passed through a sample and received by a second probe, not shown, which will transmit the light to an optical analyzer. This mode of transmission is the transmissive mode. The third mode of operation is called a transflectance mode, in which light is both reflected by a sample and transmitted through a sample. One way to accomplish this is to use a probe which receives reflected light. That light which is not reflected is passed through the sample and reflected a second time through the sample by a mirror or the like. The light which passes back through the sample is then received by the probe and transmitted through bidirectional optical fiber cables to the analyzer.

One of the great advantages of the linear multiplexer is that there are very short path lengths which the light must travel in order to reach an optical transmission rod. Since optical transmission rods 54 and 56 may be placed virtually next to the mirrored surface 48, there is little chance for error due to misalignment of the transverse probe 46.

The foregoing description of the preferred embodiments of the invention has been presented for purposes of illustration and description. It is not intended to be exhaustive or to limit it to the precise form disclosed. Obviously, many modifications and variations may be made in light of the above teachings.

The embodiments were chosen and described in order to best explain the principles of the invention and its practical application to thereby enable others skilled in the art to best utilize the invention in various embodiments and with various modifications as are suited to the particular use contemplated. For example, the multiplexer of the present invention has been described with particular reference to multiplexing light to be used to analyze samples with an electro-optical device; however, the concepts of the invention could be adapted to other technologies such as those technologies found in the communications field. It is intended that the scope of the invention be defined by the claims appended hereto.

What is claimed is:

1. A multiplexer for introducing light to multiple samples, comprising
    a body portion, said body portion including a primary inlet port for receiving a stream of light;
    a conjugate optical barrel, said conjugate optical barrel being rotatably attached to said body portion;
    means for reflecting the stream of light passing through said primary inlet port at an angle;
    said body portion having an exit port oriented to selectively receive light reflected by said means for reflecting; and
    an inlet port for receiving light down stream of said exit port; the conjugate optical barrel further comprising means for reflecting the stream of light through a primary exit port.

2. The multiplexer of claim 1 wherein said body portion has a plurality of pairs of inlet and outlet ports whereby rotation of said conjugate optical barrel selectively activates one of said plurality of pairs of inlet and outlet parts for passing light to and from a sample to be analyzed.

3. The multiplexer of claim 2 further comprising a motor for rotating said conjugate optical barrel relative to said body portion.

4. The multiplexer of claim 3 wherein said motor rotates said conjugate optical barrel.

5. The multiplexer of claim 3 wherein said motor is a stepper motor.

6. The multiplexer of claim 3 further comprising an optical encoder.

7. A linear multiplexer, comprising:
    (a) a transverse probe, said probe having means to receive light and to transmit light at an angle;
    (b) first means for selectively receiving light transmitted from said probe;
    (c) second means for selectively receiving light transmitted from said probe; and
    (d) a stepper motor for precisely and selectively positioning said transverse probe relative to at least said first means for selectively receiving light transmitted from said probe.

8. The linear multiplexer of claim 7 wherein said transverse probe comprises an optical rod having an angled reflective end.

9. The linear multiplexer of claim 8 wherein said first means for selectively receiving light from said probe comprises a first optical rod.

10. The linear multiplexer of claim 9 wherein said second means for selectively receiving light from said probe comprises a second optical rod.

11. The linear multiplexer of claim further comprising a motor for rotating said transverse probe to selectively transmit light to said first optical rod and said second optical rod.

* * * * *